US011179039B2

(12) United States Patent
Gregersen

(10) Patent No.: US 11,179,039 B2
(45) Date of Patent: Nov. 23, 2021

(54) DEVICE FOR DETERMINING SURFACE PROPERTIES OF HOLLOW STRUCTURES

(71) Applicant: GI Bionics LLC, San Diego, CA (US)

(72) Inventor: Hans Gregersen, Ma On Shan (HK)

(73) Assignee: GI Bionics LLC, San Diego, CA (US)

( * ) Notice: Subject to any disclaimer, the term of this patent is extended or adjusted under 35 U.S.C. 154(b) by 779 days.

(21) Appl. No.: 15/520,367

(22) PCT Filed: Feb. 12, 2016

(86) PCT No.: PCT/IB2016/050751
§ 371 (c)(1),
(2) Date: Apr. 19, 2017

(87) PCT Pub. No.: WO2016/128935
PCT Pub. Date: Aug. 18, 2016

(65) Prior Publication Data
US 2017/0325688 A1 Nov. 16, 2017

(30) Foreign Application Priority Data
Feb. 13, 2015 (CN) .......................... 201510077674.6

(51) Int. Cl.
*A61B 5/00* (2006.01)
*A61B 5/01* (2006.01)
*A61B 5/20* (2006.01)

(52) U.S. Cl.
CPC .......... *A61B 5/0086* (2013.01); *A61B 5/0062* (2013.01); *A61B 5/015* (2013.01);
(Continued)

(58) Field of Classification Search
CPC ..... A61B 5/0086; A61B 5/015; A61B 5/4222; A61B 5/6853; A61B 5/0062; A61B 5/42;
(Continued)

(56) References Cited

U.S. PATENT DOCUMENTS 6,450,971 B1   9/2002   Andrus et al.
2002/0082515 A1   6/2002   Campbelli et al.
(Continued)

FOREIGN PATENT DOCUMENTS

CN   201905858 U   7/2011
CN   201912041 U   8/2011
(Continued)

*Primary Examiner* — Bo Joseph Peng
(74) *Attorney, Agent, or Firm* — Reichel Stohry Dean LLP; Mark C. Reichel; Natalie J. Dean

(57) ABSTRACT

An elongated device and a system that at the same time allow acquisition of temperature-related data of high spatial and temporal resolution from hollow structures together with other relevant data of physical or chemical variables. In a preferred embodiment infrared or visible light sensors are used to obtain thermal or color images from the inner surface during imposed change of the temperature in the lumen of the hollow structure. The disclosure makes it possible to evaluate thermal variations when the inner surface returns to pre-change thermal conditions. High-resolution data can be obtained with the disclosure. The disclosure further includes a system with rotators, injection pumps, a control unit and display operably coupled to one or more of the data acquisition and processing system.

16 Claims, 3 Drawing Sheets

(52) U.S. Cl.
CPC .......... *A61B 5/4222* (2013.01); *A61B 5/6853* (2013.01); *A61B 5/20* (2013.01); *A61B 5/42* (2013.01); *A61B 5/4233* (2013.01); *A61B 2562/0276* (2013.01)

(58) Field of Classification Search
CPC .. A61B 5/4233; A61B 5/20; A61B 2562/0276
See application file for complete search history.

(56) References Cited

U.S. PATENT DOCUMENTS

| | | | |
|---|---|---|---|
| 2002/0168317 A1* | 11/2002 | Daighighian | A61K 49/18 424/1.11 |
| 2003/0171691 A1* | 9/2003 | Casscells, III | A61B 5/0075 600/549 |
| 2007/0078500 A1 | 4/2007 | Ryan et al. | |
| 2008/0033519 A1* | 2/2008 | Burwell | A61N 5/062 607/122 |
| 2015/0011843 A1* | 1/2015 | Toth | A61N 1/36185 600/301 |

FOREIGN PATENT DOCUMENTS

| | | |
|---|---|---|
| CN | 201912043 U | 8/2011 |
| CN | 201929931 U | 8/2011 |
| CN | 103442631 A | 12/2013 |
| CN | 104720752 A | 6/2015 |
| CN | 204445838 U | 7/2015 |

\* cited by examiner

DEVICE FOR DETERMINING SURFACE PROPERTIES OF HOLLOW STRUCTURES

RELATED APPLICATIONS

The present invention claims the benefit of priority from Chinese Patent Application No. 201510077674.6 filed on 13 Feb. 2015, the disclosure of which is incorporated herein in its entirety by reference.

FIELD

The present disclosure relates to devices for monitoring and determining surface properties of a hollow structure, and particularly a device for determining thermal surface property of a hollow structure and a system comprising the same.

BACKGROUND

It is of interest to study the material properties including the inner and outer surfaces of hollow structures such as pipes, tubes, cones, spheres and other geometries. Such structures can be designed by engineers or by nature, and they can be made of biological or non-biological materials. In the remaining document the term "pipe" is used in general for these structures but pipe should be understood in a broad sense and include any hollow structure of any geometry, either engineered or made by nature. Pipes have many chemical and physical properties including thermal properties of their surfaces. Thermal measurements are of interest since they can be used to detect damage, weakness, and leakage of the pipe and temperature variations on the surface. The thermal properties of a surface can be detected using thermal cameras based on detection of infrared radiation. A practical application of thermal cameras is to detect leakage of heat from poorly insulated houses or to search for warm objects in nature (often in military equipment). Thermal cameras can also be used to detect leakage of pipes but such measurements are often done from the outside, which may not be possible if the pipe is embedded or its outer surface is somehow not accessible. In the medical field infrared thermal cameras are now finding use in studying the body surface and thermal properties of the skin.

It is of considerable interest to measure the thermal properties of the inner surface in engineered pipes to detect leakage problems and other types of materials or surface defects since the weaknesses may arise first at the inner surface. It is also of interest to measure the thermal properties including leakage in biological tubes. One example of a biological tube is the gastrointestinal tract that serves to transport nutrients and fluids from the mouth to the site where they are being absorbed in the intestines. Food and liquids are swallowed and transported from the mouth through the pharynx and esophagus to the stomach for further breakdown before entering the small intestine. The ingested material that is not absorbed will, together with secretions from the gastrointestinal mucosa, be expelled from the large intestine and rectum in liquid or solid form.

Various diseases of the esophagus and the intestines disturb or inhibit the function which may give rise to symptoms. Common gastrointestinal diseases are inflammatory diseases, precancer and cancer. Such diseases can be difficult to diagnose with conventional diagnostic tools and medical imaging technologies. However, these diseases are all characterized by increased cell metabolism which increases the energy production in the cells. This energy is dissipated as heat in the tissues and may cause local increase in temperature.

Pipes are often used to transport cold or warm fluids and often have insulation materials to prevent energy to dissipate during the fluid transport in the pipe. However, some kind of damage may arise in the pipe during the construction process or during long-term use or breakdown of the materials. For example, a pipe made of iron will slowly erode. Before fluid actually starts to leak, the pipe will show weaknesses that can be measured as thermal variations on the surface of the structure. However, the pipe may not always be accessible from the outside and therefore it is necessary to develop solutions where the pipe can be studied from the inside.

The physical properties including the thermal properties are also of importance in biological pipes or tubes. The gastrointestinal tract is of special interest since it is a 6-10-meter-long tube where the temperature can vary locally due to several reasons. For example the inner surface of the esophagus is cooled down or heated up by drinking cold or warm drinks. Also inflammatory processes and cancer in the tissue may cause local energy dissipation and heating of the tissue. Patients with gastrointestinal symptoms will usually have tests done on gastrointestinal function. These tests are usually done in gastrointestinal motility laboratories by a specialized technician or nurse. The most widely used tests of the esophagus are high-resolution manometry (HRM), pH-recordings, and endoscopy.

Gastrointestinal stimulation tests were developed during recent years. These tests are based on mechanical stimulation by balloon or bag distension, by acid infusion or by other stimulation methods. For simplification the term bag distension is used in the rest of this disclosure, knowing that the balloon or bag for distension may be made of many different and known materials and also may have a certain defined size or be stretchable. However, new technology that tests other properties is greatly needed, especially technology that uses different approaches than the conventional technologies based on pressure recordings, endoscopy, and magnetic resonance imaging.

In respect of the above considerations, new devices, systems, and methods for obtaining better and more detailed data/information on pipes and biological tubes will be welcome.

Chinese utility model patents CN201929931, CN201912043, CN201912041, CN201905858, and other closely related Chinese patents describe a medical capsule enteroscopy system capable of entering the small intestine for examination. It provides a capsule type enteroscopy system with infrared thermal scanning function wherein a receiving lens receives infrared rays radiated from the digestive tract. The limitation of such a system is that it contains a very limited number of infrared light sensors (often only uni-directional or bi-directional at the two ends in longitudinal direction), the orientation of the capsule inside the digestive tract cannot be controlled and the capsule passes some parts of the gastrointestinal tract, for example the esophagus, too fast to make meaningful recordings.

DISCLOSURE

The present invention is a device that manages to measure surface properties inside circular or non-circular pipes. Different embodiments of the present invention provide different solutions for obtaining various data, such as thermal data. Common for the embodiments is an elongated tube, a catheter with any kind of colour/thermal sensing system mounted. The tube contains wires or fibers for transmitting imaging data or other data from the sensors to the external equipment. In some embodiments, the sensor will be placed inside a bag filled with fluid, such as air or gas of any kind. The novelty lies in that the gas inside the bag can be used temporarily to change the temperature of the surface. Hereby, variations in thermal properties across the surface may become more apparent. Some embodiments may also incorporate various means such as lenses to improve or direct the signals. A preferred embodiment provides a system that uses sensors for infrared light, light of near-infrared (Raman) wave lengths or other wave lengths to obtain data on physical properties such as temperature. This embodiment as well as other embodiments may be combined with a variety of other measurements from the elongated tube such as pressure recordings, chemosensors like ammonium or pH-sensors, electrical impedance recordings, and imaging technologies. The specific idea is to evaluate physical or chemical properties of a hollow structure like a pipe or tube but needless to say the invention may also be used for purposes outside pipes and in non-pipe structures. However, the preferred use relates to a device for the measurement of thermal properties of the inner surface of a pipe. The unique idea of the present invention is that the wavelength/colour/thermo-sensing elements are located on a finite length tube wherein the position of each element can be controlled inside the tube. The surface properties, such as the thermal surface properties, can be detected by various means incorporated into the elongated tube. In some embodiments, which make use infrared or near-infrared sensors and effect detection of color change in materials that change color with temperature but these embodiments are just exemplary rather than limitative. Ideally the device should measure from many locations at the same time and gather data from the whole inner surface of the tube, in other words, the device is to get circumferential data. One embodiment uses infrared light sensors that measures the total circumference or part of the circumference of a hollow pipe with high resolution. The position of the sensors can be controlled, and warm and cold fluid such as gas can be applied inside a bag or without a bag to stimulate a reaction of the pipe and how it returns to the pre-stimulation temperature. The cold or warm stimuli can be applied by perfusion of the pipe with cold or warm fluid, by heating the pipe from outside or heating it from one end or both ends, or by distending a bag inside the pipe with fluid that will change the temperature of the pipe wall temporarily or more permanently. The preferred fluid is a gas since gas will allow the infrared light to transmit from the surface to the sensors but any type of fluid may be used in the system. The disclosure further discloses a system with a display operably coupled to one or more of the data acquisition and processing system. For clarification the term "thermal imaging sensor" cover a variety of embodiments with sensors capable of detecting the thermal proepties of a surface. The present disclosure is not limited to infrared sensors or use of materials that changes color with temperature.

FIGURES

The various embodiments and other features, advantages, and disclosures contained herein will become apparent and the present disclosure will be better understood by reference to the following description of various preferred embodiments of the present disclosure taken in conjunction with the accompanying drawings, wherein.

DESCRIPTION

The present disclosure provides an elongated device and a system that at the same time allow acquisition of temperature-related data of high spatial and temporal resolution from hollow structures together with other relevant data of physical or chemical variables. In some embodiments, infrared or visible light sensors are used to obtain thermal or color images from the inner surface during imposed change of the temperature in the lumen of the hollow structure. The disclosure makes it possible to evaluate thermal variations when the inner surface returns to pre-change thermal conditions. High-resolution data can be obtained with the disclosure. The disclosure further comprises a system with rotators, injection pumps, a control unit and display operably coupled to one or more of the data acquisition and processing system.

Figure 1A:
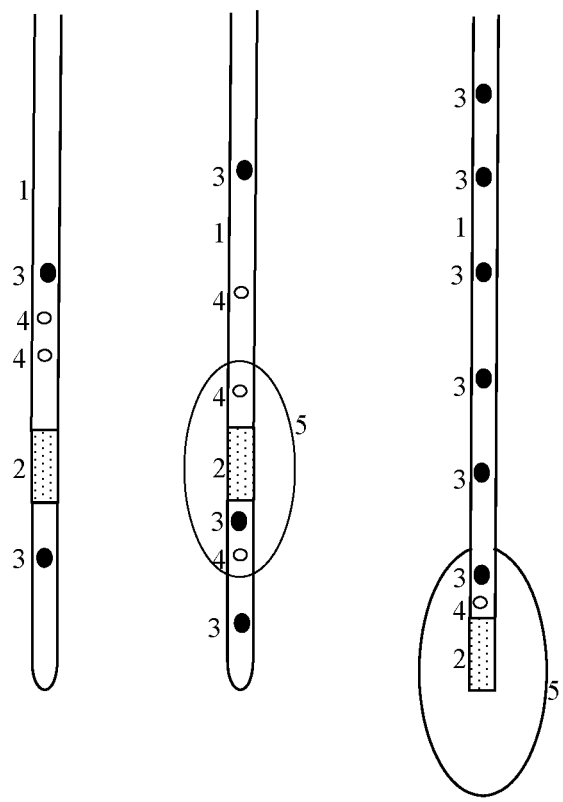
FIG. 1A are schematic views showing various configuration of devices for determining surface properties of a hollow structure according to embodiments of the present disclosure.
Figure 1B:
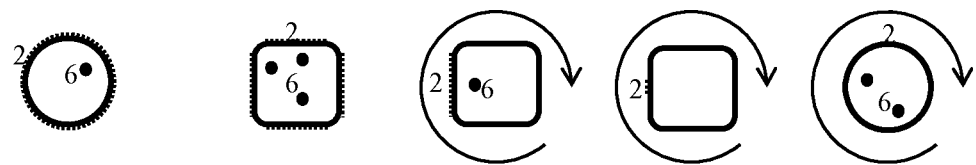
FIG. 1B are cross sectional schematic views showing various configuration of devices for determining surface properties of a hollow structure according to embodiments of the present disclosure.

Referring to FIG. 1A, which shows three views of a portion of preferred devices with a thermal imaging sensor, a bag and a variety of other sensors mounted on an elongated body, according to a preferred embodiment of the present disclosure. FIG. 1A exhibits that the device for monitoring or determining surface properties, and preferably a thermal surface property, of a hollow structure, particularly a biological hollow structure and more particularly a gastrointestinal, genital, or urinary tract, may comprises the elongated body 1, the thermal imaging sensor and/or wavelength sensor 2, other additional sensors 3 of various type, injection channels and/or side holes 4 and a bag 5, as would be described in further details hereunder. FIG. 1B shows five different cross-sections of the device at the site of the thermal imaging sensor. FIG. 1B exhibits the thermal imaging sensor and/or wavelength sensor 2 and wires 6 on the path to other sensors. The arrow shows rotation of the device in the preferred embodiments that do not have circumferential sensors.

Figure 2:
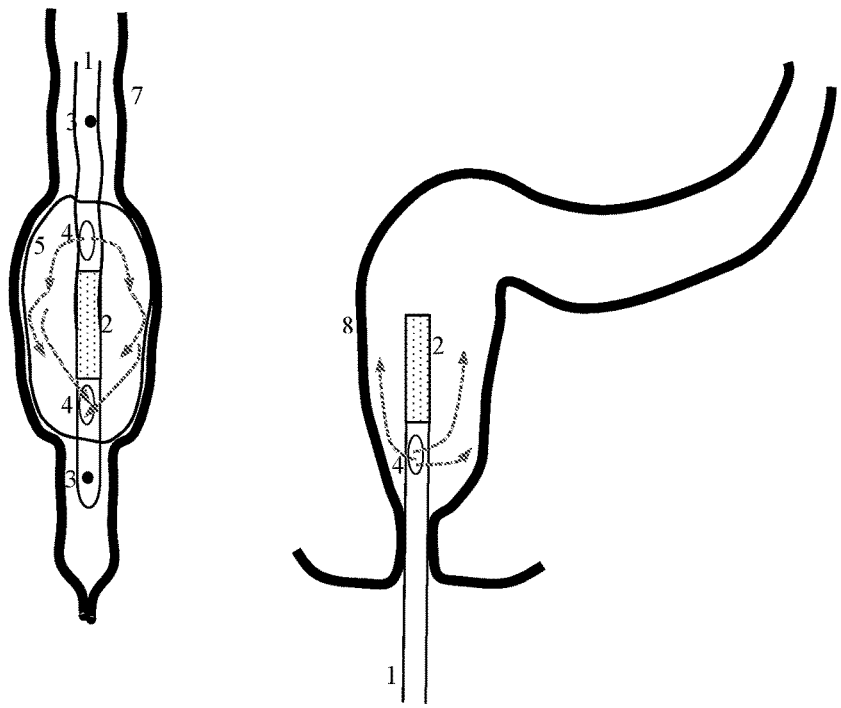
FIG. 2 are schematic views showing the flow of fluid with or without the bag of the devices for determining surface properties of a hollow structure according to embodiments of the present disclosure.

FIG. 2 shows views of a portion of two preferred devices placed in a distensible pipe like the esophagus with a bag distended and in the rectum with infusion channels for cold or warm fluid such as air, according to preferred embodiments of the present disclosure. FIG. 2 exhibits the elongated body 1, the thermal imaging sensor or wavelength sensor 2, other sensors 3, injection channels and side holes 4, a bag 5, and the wall of the pipe such as esophagus 7 or rectum 8.

Figure 3:
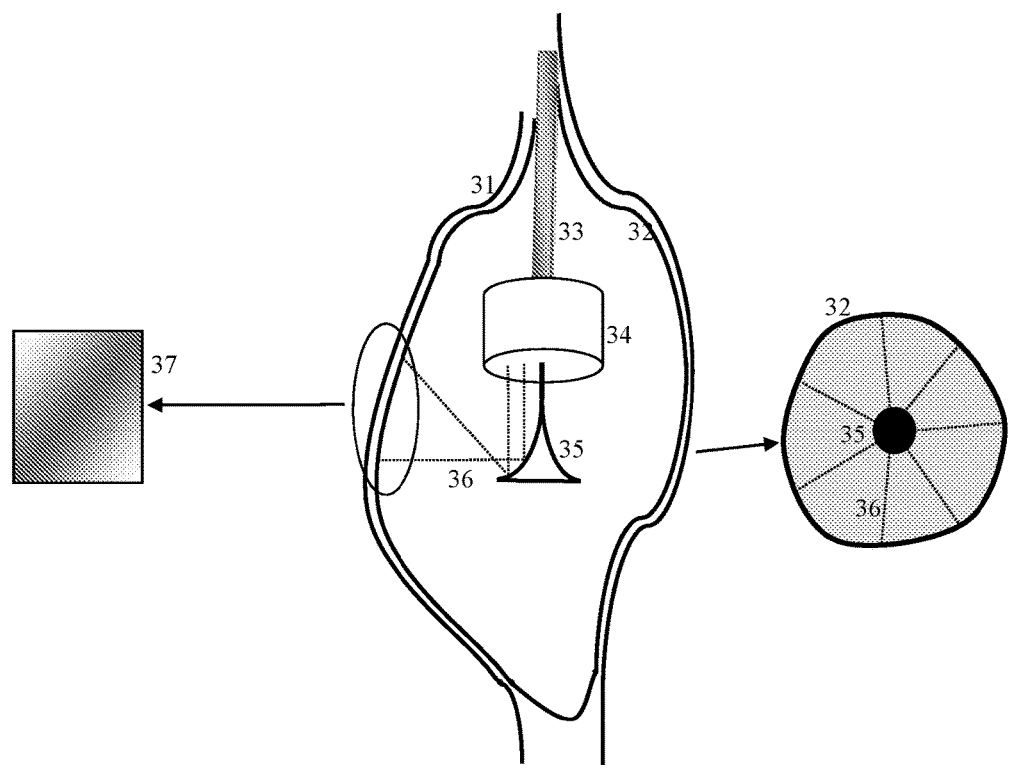
FIG. 3 are schematic views showing the redirection of lightwaves using a conical-like shaped reflective device or mirror according to other embodiments of the present disclosure.

FIG. 3 shows an embodiment wherein the light waves are redirected using a reflective device, such as a conical-like shaped reflective device or a mirror for reflection of waves. The conical-shaped device or the mirror may be driven to rotate either manually or automatically via a driving mechanism (not shown) if needed to provide image data from the entire circumference of the pipe's inner surface in case of that there is just a single wavelength sensing device. Software algorithms and/or a processing unit are used to generate a geometrically correct thermal image of the wall based on the wave reflections. FIG. 3 shows the wall of a hollow structure, such as an esophagus wall 31, and the bag wall 32 of a fully inflated bag and another exemplary device positioned inside the bag. The device of the present embodiment comprises a rotatable shaft or tube 33 (corresponds to the elongated body 1 of previous embodiments), sensor or optic fiber elements 34 (corresponds to the thermal imaging sensor or wavelength sensor 2 of previous embodiments) being in communication with at least one additional internal or external sensor (not shown) and having its one end (or proximal end) fixedly or rotatably mounted at the tube 33, and a conical-shaped reflection device 35 fixedly or rotatably connected to another end (or distal end) of the sensor or optic fiber elements 34. Waves are transmitted from the wall (illustrated as dotted lines 36) and an image is generated for the wall 37 after processing received waves from the walls 31 and/or 32 via the algorithms and/or the processing unit. The device may include a light source as well as color sensors to enable the generation of an image for determining surface property of the pipe or hollow structure via light wave in the visible range. In some embodiment, the conical-shaped device or the mirror may be fixedly arranged if there are multiple wavelength sensing elements arranged evenly about the periphery of the sensor or optic fiber elements 34, such that an image data from the entire circumference of the pipe's inner surface could be obtained without rotating the conical-shaped device or the mirror.

Figure 4:
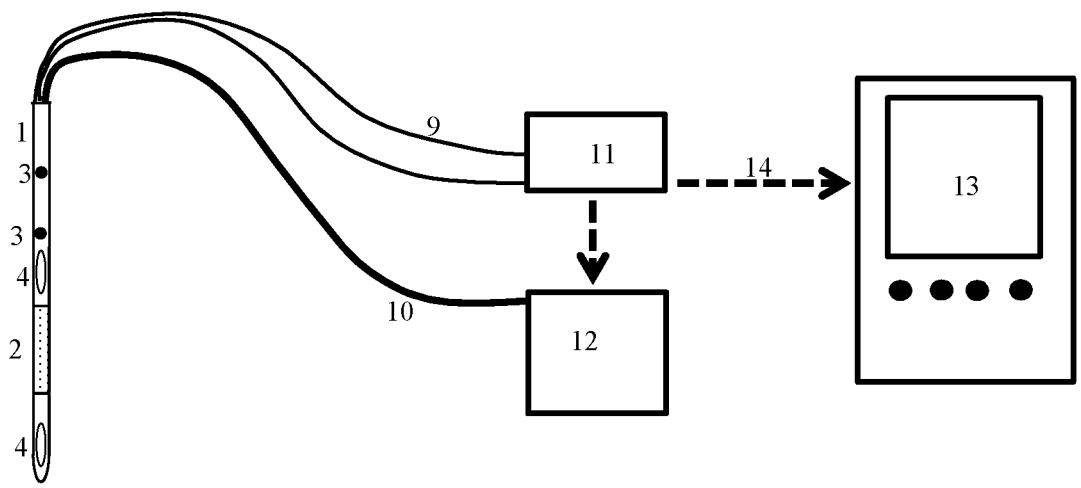
FIG. 4 is a block diagram illustrating various exemplary components of a system according to a preferred embodiment of the present disclosure.

FIG. 4 shows block diagrams of components of a system, according to a preferred embodiment of the present disclosure. FIG. 4 exhibits the elongated body 1, the thermal imaging sensor or another wavelength sensor 2, other sensors 3, injection channels and side holes 4, wires 9, connecting wires or tubes 10, a control unit 11, other devices such as pumps and rotators 12, a display or computer 13, and wired or wireless connections 14. FIG. 4 shows a preferred embodiment of the system but variations may occur, for example it may not be needed in some embodiments to have the rotator.

In some embodiments of a device of the present disclosure, the device for determining surface properties, such as a thermal surface property, of a hollow structure such as a biological hollow structure including a gastrointestinal, genital, or urinary tract, may comprises an elongated body 1, in the form of a catheter, adapted for entering into and positioning in vicinity of a target region of the hollow structure and having a length suffice to enable its distal end to extend into a pipe or extend to a person's esophagus or intestines while its proximal end, or a connector coupled thereto, is present at the person's external orifice like the mouth or anus, in the person's throat, or outside of the person's mouth and body. In some of other embodiments, both the distal and proximal ends of the elongated body are received into the hollow structure and the elongated body is in data communication with an external processing unit via a wire or cable. The device will carry a thermal imaging sensor and/or another type of wavelength sensor 2 positioned at known location along the elongated body 1. The thermal imaging sensor 2 may contain a lens if a lens is needed for focusing or filtering the incoming signals such as the infrared light waves or other waveforms. The preferred embodiment includes a thermal sensor in the infrared light wave length but in other preferred embodiments other wave lengths may be used such as near-infrared Raman wave lengths, ultrasonic wave lengths or light in the visible range of different color spectras. The device may also comprise one or more other type of sensors 3 wherein some of the sensors can measure pressure, force or biological signals. These sensors can also be imaging sensors such as endoscopic ultrasound transducers or confocal laser endoscopy that both can provide data on the wall structure such as to identify submucosal tumors. The plurality of sensors 3 may comprise thirty or more sensors. In some embodiments, the device may contains one or more channels and injection holes 4 for injection or infusion of fluid such as gas, and preferably pressurized gas. The gas may be infused directly into the pipe or into an inflatable or flexible bag 5 mounted on and enclosed at least partially the catheter. The bag 5 serves to control the distribution of the volume of the injected gas and to secure good contact with the wall of the pipe. The thin-walled bag is in some embodiments painted or sprayed with a film containing thermo-chromatic crystals or other materials, or made from a material that is thermo-sensitive by changing color or other properties such as electromechanical properties of embedded sensors or sensing elements as function of temperature. The thermo-chromatic crystals may in a preferred embodiment be embedded in the bag material. Since thermo-chromatic crystals usually only spans a narrow range of temperatures such as 5 degrees Celsius, then different crystals may be applied or mixed in order to cover a wider temperature range.

The bag is at least partially made of a flexible material and have a definite shape. It is in fluid communication with the channel/hole 4 and enclosed at least partially the elongated body 1 and/or the wavelength sensing unit/sensors 2 and 3, wherein the bag is in a non-inflated or inactive configuration and of a first shape when the elongated body and the bag are configured to enter into and remove from the target region of the hollow structure, and the bag is in an inflated or active configuration when the elongated body and the bag are positioned in the target region and the bag is filled with the fluid introduced via the channel to enable the bag to transform into a second shape or a shape substantially conform to that of the target region, such that at least a portion of outer surface of the bag is in contact with at least a portion of inner wall of the hollow structure at the target region to effect a heat exchange process between the fluid and the inner wall; and The wavelength sensing unit/sensors 2 and 3 are configured for obtaining, monitoring, determining, and comparing spatial and temporal data of a preset resolution on the surface properties of the inner wall preferably before, after, and/or throughout the heat exchange process.

In some embodiments, at least one portion of the elongated body and/or the inflatable bag is made of thermo-chromatic crystals or a material capable of changing its color or electromechanical properties with temperature. In other embodiments, at least one portion of the elongated body and/or the inflatable bag is sprayed, coated, or painted with thermo-chromatic crystals or a material that changes color with temperature; wherein changes of color of the at least one portion and/or the wall of the pipe are sensible by the wavelength sensor or a color sensor preferably with a light source arranged at the elongated body, which is to illuminate the elongated body, the wall of the pipe, and/or the inflatable bag to facilitate the monitoring of color changes thereon.

Referring again to FIG. 1A, the inflatable bag 5 is configure to surround or enclose at least one side hole 4, the thermal imaging sensor and/or wavelength sensor 2, and the additional sensor 3 of different type. In some embodiments, the bag could be configure to enclose merely one or more side holes 4, such that the thermal imaging sensor and/or wavelength sensor 2 could selectively examine, monitor and determine directly both the inner surface and outer surface properties of the bag 5 apart from determining the inner surface properties of the hollow structure.

The gas can be injected into the bag 5, recirculated or taken out of the bag 5 through one or more side holes 4 connected to one or more internal channels in the catheter. FIG. 2 shows a catheter with the infrared sensor 2 placed inside a bag 5 or without a bag with the holes 4 for injection or withdrawal of the gas. The dotted lines with arrows in FIG. 2 shows the flow of the gas between an upper hole 4 and a lower hole 4 inside the bag 5, or the flow of gas within the hollow structure or rectum 8, wherein the sensor 2 is preferably positioned between the two holes 4 or at the centre of the hollow structure under examination to ensure or maximize the accuracy and speed of data acquisition. The purpose of the gas is to allow the infrared waves or other waves to pass from the surface of interest to the sensor with minimal damping. Gas is preferable since its absorbance of infrared waves or distortion of other waves is low. Another advantage of injection of gas is that the temperature of the gas can be controlled at lower or higher temperatures than the fluid in the pipe. The gas induces a temperature change in the wall and the properties of the pipe wall can be evaluated. For example, if the pipe is the esophagus of a person, then cold air will cool the inner mucosal surface of the esophagus. After stopping the injection, the temperature of the mucosa will increase back to body temperature. The temporal and spatial characteristics of the temperature change are of importance, for example if the temperature increase is fast, then the mucosa has a good blood perfusion whereas slower temperature increase indicates less perfusion. If it is too fast it may indicate that the tissue is inflamed and with high perfusion. Spatial variations will likely be evident, for example one spot may exhibit faster temperature change if the tissue is inflamed or irritated by injection of a chemical or if a tumor is located beneath the surface due to the high metabolism in tumors. Needless to say temperature differences may be created in other ways, for example by cooling or heating the pipe from outside, or as an example again for the esophagus, it is desirable to let the person drink cold or hot fluids that will change the temperature in the esophagus and its wall temporarily. The gas may also be injected through a separate elongated body or pipe/tube adapted for entering into and positioning in vicinity of a target region of the hollow structure, such as the esophagus.

In a preferred embodiment of a device of the present disclosure, the infrared thermal sensor or wavelength sensor 2 is cylindrical as shown in the left schematic in FIG. 1B. In this preferred embodiment infrared thermal data can be obtained on a continuous basis from the whole circumference for a given length of the sensor. The sensor can be from few mm long to many cm long and may contain up to millions of infrared sensing elements. The sensor 2 can have any other shape than a cylinder in the preferred embodiments. FIG. 1B shows, in addition to the cylindrical sensor, several other cross-sections of sensor geometries such as squared with sensing elements on all four sides or with sensing elements covering one side only. The infrared sensor may merely consist of one of more sensing elements as shown in the three right figures in FIG. 1B. Since infrared sensors with other geometries than the cylindrical geometry cannot measure in the whole circumference of the pipe, then a preferred embodiment may contain a device that can rotate the infrared sensor 2 or even rotate the entire elongated body 1. A 360 degree rotational thermal view can then be generated using algorithms and control/processing unit. Postprocessing can also reveal the thermal imaging views as function of time and various parameters can be calculated in addition to the display of the thermal images. The cross sections of the sensor 2 part of the elongated body 1 illustrated in FIG. 1B also show one or more wires to the sensing elements in the infrared sensor or to other sensors.

In a preferred embodiment of use of the present disclosure, the method comprises the steps of inserting at least part of a preferred device as described herein of the present disclosure into a non-biological pipe or into a biological pipe like a person's gastrointestinal tract, esophagus, or intestines, and operating the device to obtain data from the lumen and wall of the gastrointestinal tract, esophagus, or intestines during imposed change of the temperature effected by injection and removal of a fluid capable of exchanging heat with the lumen and wall. With new microsensors and nanotechnology method and device of the present disclosure may also be adapted to and applicable in smaller organs such as in the urinary tract or in the vagina without loss of generality.

The present disclosure also includes disclosure of various systems as shown in the block diagram of FIG. 4. As shown in the figure, a preferred system for monitoring or determining surface properties of a hollow structure including biological hollow structure, such as a gastrointestinal, genital, or urinary tract, of the present disclosure comprises a elongated body 1 adapted for entering into and positioning extended into and positioned rotatably in vicinity of a target region of the hollow structure and provided with infrared sensing/wavelength sensing unit or sensor 2 configured for obtaining spatial and temporal data on the surface properties of the target region of the hollow structure, other type of sensors 3 for sensing other environmental conditions or data, and injection channels and side holes 4 configured for introducing and expelling a fluid and connected through wires 9 to a control/processing device 11 for controlling the sensors and conditioning of signals. The system may also comprise one or more pumps for facilitating the injection of the fluid or a rotator unit 12 for rotating the sensors 2 and/or the elongated body 1 if needed. The display or the computer 13 contains a storage medium to store data for real-time or off-line analysis.

While various embodiments of the device and systems with high resolution data recording of various signals have been described in considerable detail, the embodiments are merely offered as non-limiting examples of the disclosure described. It will therefore be understood that various changes and modifications may be made, and equivalents may be substituted for elements thereof, without departing from the teachings, essence, and scope of the present disclosure. The present disclosure is not intended to be exhaustive or limiting with respect to the content thereof.

Figure 5:
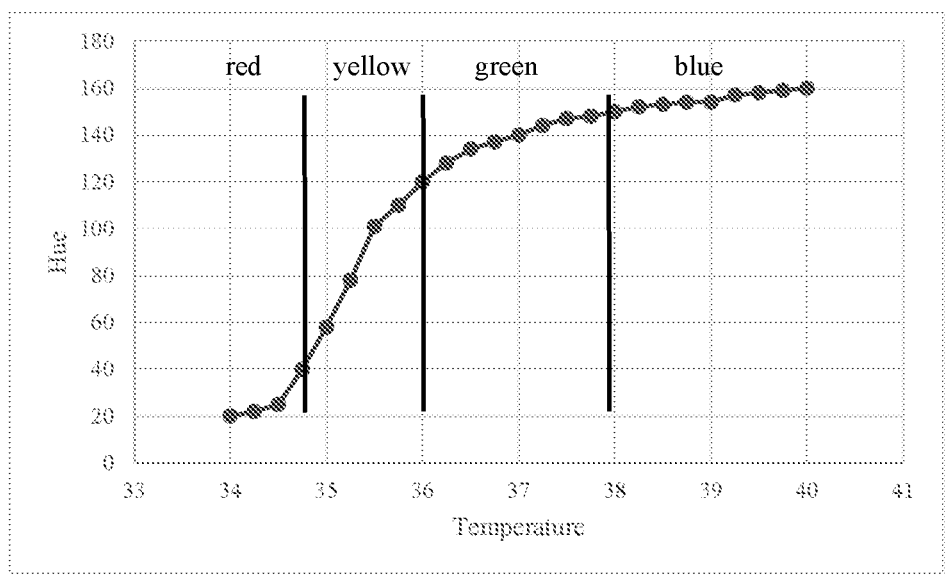
FIG. 5 is a line chart illustrating exemplary temperature resolution of thermo-chromatic crystals employed by a device for determining surface properties of a hollow structure according to another embodiment of the present disclosure.

The device of the present disclosure may in practice and theory be of any size but for applications in the human esophagus, a length of 2-3 cm and a diameter of the tube and sensor of less than 1 cm will be preferable. The spatial resolution ideally will be around 1 mm² (the pixel size) but can be higher or lower, depending among other factors on the number of sensor elements. The temperature measurement resolution is ideally 0.25 degree Celsius with data being obtained at a frequency of 10 Hz. The whole temperature span to be covered by the system will, for human applications, be between 5-60 degrees Celsius, in most cases between 20-50 degrees Celsius. In some embodiments, which showed that a five degree Celsius temperature change was measured in less than half second which was found to be sufficient but ideally can be improved. In some embodiments as depicted by FIG. 5, the use of thermo-chromatic crystals sprayed on a 25 microns thick PU bag provides a temperature resolution that is acceptable for the application. Validation has also been obtained for safety purposes in human subjects where a 5 mm OD tube with sensors mounted was used. The inflatable bag had a maximum size of 4 cm and could readily be distended to 2.5-3 cm inside the human esophagus without causing significant pain. The bag distension can be maintained for several minutes. This allows enough time for the thermal studies.

Features set out in the claims hereto (jointly and severally where appropriate) are to form part of this disclosure and are incorporated herein by reference.

While various examples or embodiments have been described herein, it should be appreciated that they are for illustration and are not for scope restriction. It should be appreciated that portions or parts of the various example embodiments can be excerpted for combination and/or mix-and-match where appropriate to form other variants without loss of generality.

The invention claimed is:

1. A device for determining surface properties, comprising:
    an elongated body adapted for entering into and positioning in a vicinity of a target region of a hollow biological structure, and
    a wavelength sensing unit fixedly or rotatably connected to the elongated body, the wavelength sensing unit selected from the group consisting of a cylindrical sensing unit configured to obtain 360 degree data within the hollow biological structure, a square shaped sensing unit having sensing elements on all four sides so to obtain 360 degree data within the hollow biological structure, and a square shaped sensing unit having sensing elements on only one side so that the square shaped sensing unit is configured to obtain 360 degree data when the hollow biological structure when rotated;
    wherein the elongated body defines at least one channel therethrough, the at least one channel configured for communication with an external source for introducing a fluid or gas from the external source into the at least one channel and out of one or more side holes defined within the elongated body;
    wherein when the one or more side holes are not surrounded by or enclosed within an inflatable bag or balloon coupled to the elongated body, the fluid or gas can exit the one or more side holes into a hollow biological structure to change a temperature of an inner surface of the hollow biological structure, whereby the fluid or gas exits the one or more side holes adjacent to and past the wavelength sensing unit so that the fluid or gas occupies a space adjacent to the wavelength sensing unit and whereby said fluid or gas can flow toward a distal end of the device; and
    wherein when the one or more side holes are surrounded by the inflatable bag or balloon coupled to the elongated body, the fluid or gas can exit the one or more side holes into the bag or balloon to inflate the inflatable bag or balloon causing the inflatable bag or balloon to contact the surface of the hollow biological structure to change the temperature of the inner surface of the hollow biological structure;
    wherein the wavelength sensing unit is configured for obtaining spatial and temporal data on the surface properties of the target region of the hollow biological structure sufficient to distinguish between various blood perfusion levels at the target region when the one or more side holes are surrounded by the inflatable bag or balloon; and
    wherein the wavelength sensing unit is configured for operation while the fluid or gas occupies the space adjacent to the wavelength sensing unit.

2. The device according to claim 1, wherein the wavelength sensing unit comprises at least one infrared sensor for obtaining thermal images of the target region of the hollow biological structure and/or a color sensor for monitoring color changes on the target region of the hollow biological structure and/or at least one fiber optic cable for transmitting or redirecting light wave from the target region to at least one external wavelength sensing unit.

3. The device according to claim 1, further comprising a reflective device, including a conical-like shaped reflective device or a mirror, fixedly or rotatably connected to the wavelength sensing unit for reflecting or redirecting light waves received from the target region of the hollow biological structure to the wavelength sensing unit or at least one additional wavelength sensing unit via at least one fiber optic cable in communication with the additional wavelength sensing unit.

4. The device according to claim 1, wherein the fluid or gas serves to act as an optimal medium for transmission of waves and signals from the inner surface of the hollow biological structure to the wavelength sensing unit and for changing the temperature of the inner surface.

5. The device according to claim 1, wherein at least a portion of the elongated body a comprises a material or a film containing thermo-chromatic crystals capable of changing its color or electromechanical properties with temperature; and/or at least a portion of the elongated body is sprayed, coated, or painted with the material or the film that changes color with temperature.

6. The device according to claim 1, wherein when the inflatable bag or balloon is coupled to the elongated body, at least a portion of the inflatable bag or balloon comprises a material or a film containing thermo-chromatic crystals capable of changing its color or electromechanical properties and/or electromechanical properties of one or more sensing elements enclosed in the bag or balloon with temperature; and/or at least a portion of the inflatable bag or balloon is sprayed, coated, or painted with the material or the film that changes color with temperature.

7. The device according to claim 1, wherein the wavelength sensing unit comprises a plurality of infrared sensors spaced apart a preset distance from one another for obtaining thermal images of the target region of the hollow biological structure.

8. The device according to claim 1, further comprising an item selected from the group consisting of lenses and reflective structures, which are arranged at the elongated body for focusing, filtering, or directing incoming signals for the wavelength sensing unit.

9. The device according to claim 1, further comprising one or more additional sensors positioned along the elongated body and configured to obtain pH data and/or predetermined chemical-related data, measure position and acceleration data, obtain potential difference data, obtain pressure data, and/or obtain electrical impedance data.

10. A device for determining a thermal surface property of a hollow biological structure, comprising:
an elongated body adapted for entering into and positioning in a vicinity of a target region of the hollow biological structure, and
a wavelength sensing unit fixedly or rotatably connected to the elongated body, the wavelength sensing unit selected from the group consisting of a cylindrical sensing unit configured to obtain 360 degree data within the hollow biological structure, a square shaped sensing unit having sensing elements on all four sides so to obtain 360 degree data within the hollow biological structure, and a square shaped sensing unit having sensing elements on only one side so that the square shaped sensing unit is configured to obtain 360 degree data when the hollow biological structure when rotated;
wherein the elongated body defines at least one channel therethrough, configured such that its distal end is connected to or embedded in the elongated body and configured such that its proximal end is in fluid communication with an external source for introducing a fluid or gas of a preset pressure and temperature;
a flexible bag or balloon in fluid communication with the at least one channel and enclosing at least partially the elongated body and/or the wavelength sensing unit, wherein the bag or balloon is in a non-inflated or inactive configuration and of a first shape when the elongated body and the bag or balloon are configured to enter into and be removed from the target region of the hollow biological structure, and the bag or balloon is in an inflated or active configuration when the elongated body and the bag or balloon are positioned in the target region and the bag or balloon is filled with the fluid or gas introduced via the at least one channel and out of one or more side holes defined within the elongated body to enable the bag or balloon to transform into a second shape or a shape substantially that conforms to that of the target region, such that at least a portion of outer surface of the bag or balloon is in contact with at least a portion of an inner wall of the hollow biological structure at the target region to effect a heat exchange process between the fluid or gas and the inner wall; and
wherein the wavelength sensing unit is configured for obtaining spatial and temporal data of a preset resolution on the thermal surface property of the inner wall preferably, sufficient to distinguish between various blood perfusion levels at the target region, when the one or more side holes are surrounded by the inflatable bag or balloon, before, after, and/or throughout the heat exchange process; and
wherein the wavelength sensing unit is configured for operation while the fluid or gas occupies the space adjacent to the wavelength sensing unit.

11. The device according to claim 10, wherein the bag or balloon is painted, coated or sprayed with a film containing thermo-chromatic crystals; or made from a thermosensitive material capable of changing color or other properties including electromechanical properties of enclosed sensing unit or sensing elements as function of temperature.

12. The device according to claim 10, further comprising a reflective device, including a conical-like shaped reflective device or a mirror, fixedly or rotatably connected to the wavelength sensing unit for reflecting or redirecting light waves received from the target region of the hollow biological structure to the wavelength sensing unit to get circumferential thermal data or 360 degree rotational thermal view of the target region.

13. A system for determining surface properties of a hollow biological structure, comprising the device according claim 1, and a stimulatory system comprising a pump for injection of the fluid or gas, and a data acquisition and processing system operably coupled to the device and configured to obtain and process data from the device and data from the hollow biological structure.

14. The system according to claim 13, further comprising a display operably coupled to the data acquisition and processing system, the display configured to visually depict measured or computed data.

15. A system for determining surface properties of a hollow biological structure, comprising the device according claim 10, and a stimulatory system comprising a pump for injection of a fluid or gas, and a data acquisition and processing system operably coupled to the device and configured to obtain and process data from the device and data from the hollow biological structure.

16. The system according to claim 15, further comprising a display operably coupled to the data acquisition and processing system, the display is configured to visually depict measured or computed data.

* * * * *